United States Patent
Shafiee et al.

(10) Patent No.: US 12,376,784 B2
(45) Date of Patent: Aug. 5, 2025

(54) AUTOMATED EVALUATION OF QUALITY ASSURANCE METRICS FOR ASSISTED REPRODUCTION PROCEDURES

(71) Applicants: THE BRIGHAM AND WOMEN'S HOSPITAL, INC., Boston, MA (US); THE GENERAL HOSPITAL CORPORATION, Boston, MA (US)

(72) Inventors: Hadi Shafiee, Boston, MA (US); Charles Bormann, Winchester, MA (US); Manoj Kumar Kanakasabapathy, Boston, MA (US); Prudhvi Thirumalaraju, Watertown, MA (US)

(73) Assignees: THE BRIGHAM AND WOMEN'S HOSPITAL, INC., Boston, MA (US); THE GENERAL HOSPITAL CORPORATION, Boston, MA (US)

( * ) Notice: Subject to any disclaimer, the term of this patent is extended or adjusted under 35 U.S.C. 154(b) by 556 days.

(21) Appl. No.: 17/640,668

(22) PCT Filed: Sep. 8, 2020

(86) PCT No.: PCT/US2020/049685
§ 371 (c)(1),
(2) Date: Mar. 4, 2022

(87) PCT Pub. No.: WO2021/046521
PCT Pub. Date: Mar. 11, 2021

(65) Prior Publication Data
US 2022/0330884 A1    Oct. 20, 2022

Related U.S. Application Data

(60) Provisional application No. 62/897,053, filed on Sep. 6, 2019, provisional application No. 62/897,049, filed
(Continued)

(51) Int. Cl.
*A61B 5/00* (2006.01)
*G06T 7/00* (2017.01)

(52) U.S. Cl.
CPC .......... *A61B 5/4343* (2013.01); *G06T 7/0014* (2013.01); *G06T 2207/20081* (2013.01);
(Continued)

(58) Field of Classification Search
CPC ............... A61B 5/4343; G06T 7/0014; G06T 2207/20081; G06T 2207/20084;
(Continued)

(56) References Cited

U.S. PATENT DOCUMENTS

2010/0291664 A1   11/2010   Herbert et al.
2012/0009156 A1   12/2012   Izadyar et al.
(Continued)

FOREIGN PATENT DOCUMENTS

CN   108986901 A   12/2018
CN   109584211 A   4/2019
(Continued)

OTHER PUBLICATIONS

CN Office Action for corresponding CN Application No. 202080068896.0, dated Jul. 30, 2024, 30 pages.
(Continued)

*Primary Examiner* — Christopher Wait
(74) *Attorney, Agent, or Firm* — Tarolli, Sundheim, Covell & Tummino LLP (57) ABSTRACT

Systems and methods are provided for assigning a quality parameter to a reproductive cellular structure. An image of the reproductive cellular structure is obtained. The image of the reproductive cellular structure is provided to a neural network to generate a value representing a morphology of the reproductive cellular structure. The value is compared to a predefined standard to provide a quality assurance metric
(Continued)

representing one of a medical personnel, a facility, a growth medium, and an identity of the reproductive cellular structure.

6 Claims, 5 Drawing Sheets

Related U.S. Application Data on Sep. 6, 2019, provisional application No. 62/897,045, filed on Sep. 6, 2019, provisional application No. 62/897,043, filed on Sep. 6, 2019.

(52) U.S. Cl.
CPC ............... *G06T 2207/20084* (2013.01); *G06T 2207/30044* (2013.01)

(58) Field of Classification Search
CPC . G06T 2207/30044; G06T 2207/10056; G06T 2207/30024
See application file for complete search history.

(56) References Cited

U.S. PATENT DOCUMENTS

| | | | | |
|---|---|---|---|---|
| 2016/0078275 | A1* | 3/2016 | Wang | G06V 10/774 382/133 |
| 2019/0162712 | A1 | 5/2019 | Wu et al. | |

FOREIGN PATENT DOCUMENTS

| | | |
|---|---|---|
| EA | 25172 B9 | 3/2017 |
| EP | 3456812 A1 | 3/2019 |
| JP | 201997425 | 6/2019 |
| WO | 2007049078 A1 | 5/2007 |
| WO | 2017221597 A1 | 12/2017 |
| WO | WO 2019/068073 | 4/2019 |
| WO | WO-2019068073 A1 * | 4/2019 ........... G06T 7/0012 |

OTHER PUBLICATIONS

Russian Office Action dated Jul. 13, 2023 referencing Application 2022108660/07(017926); Applicant(s) The Brigham and Women's Hospital, Inc., The General Hospital Corporation, pp. 1-4.
PCT Search Report and Written Opinion for corresponding Application Serial No. PCT/US 20/49685, mailed Dec. 3, 2020, pp. 1-9.
Official Notification of JP Final Office Action and English translation issued on Dec. 4, 2023, pp. 1-5.
Japanese Office Action dated Mar. 31, 2023, pp. 1-4.
Khosravi, Pegah, et al. "Deep learning enables robust assessment and selection of human blastocysts after in vitro fertilization." NPJ digital medicine 2.1 (2019): 1-9.
European Search Report for Corresponding Application Serial No. EP 20860701, Dated Apr. 10, 2022, pp. 1-41.
Intellectual Property Office of Singapore Written Opinion for corresponding Application No. 11202202069Q, Application filing date Aug. 9, 2020, date of Written Opinion May 12, 2023, pp. 1-9.
Canadian Office Action dated Mar. 21, 2023, pp. 1-3.
2nd Canadian Office Action, PT215787CA, dated Jan. 16, 2024, pp. 1-3.
Russian Office Action for Corresponding Application Serial No. 2022108660/28, Dated Dec. 28, 2022, pp. 1-6.
Russian Search Report for Corresponding Application Serial No. 2022108660/28, Dated Dec. 28, 2022, pp. 1-3.
Communication pursuant to Article 94(3) EPC regarding examination of Application No. 20860 701.0-1207, dated Mar. 6, 2025, 7 pages.
Office Action—Korean Intellectual Property Office dated Mar. 20, 2025, 4 pages.
Pegah Khosravi, "Deep learning enables robust assessment and selection of human blastocysts after in vitro fertilization", NPJ Digital Medicine, vol. 2, No. 1, Apr. 2019, Scripps Research Translational Institute, 9 pages.

* cited by examiner

AUTOMATED EVALUATION OF QUALITY ASSURANCE METRICS FOR ASSISTED REPRODUCTION PROCEDURES

CROSS-REFERENCE TO RELATED APPLICATIONS

This application is a national phase application of and claims priority from PCT International Patent Application PCT/US2020/049685, filed Sep. 8, 2020. which claims the benefit of U.S. Provisional Application No. 62/897,043 filed Sep. 6, 2019 entitled "DEEP NEURAL NETWORK-ENABLED EMBRYO TRACKING AND SPECIMEN IDENTIFICATION SYSTEM FOR ERROR MINIMIZATION IN IVF PRACTICES," U.S. Provisional Patent Application Ser. No. 62/897,045 filed Sep. 6, 2019 entitled "AUTOMATED QUALITY ASSESSMENT OF INDIVIDUAL EMBRYOLOGISTS PERFORMING ICSI USING DEEP LEARNING-ENABLED FERTILIZATION AND EMBRYO GRADING TECHNOLOGY," U.S. Provisional Patent Application Ser. No. 62/897,049 filed Sep. 6, 2019 entitled "MONITORING OF HUMAN EMBRYO CULTURE CONDITIONS USING A DEEP LEARNING-DERIVED KEY PERFORMANCE INDICATOR (KPI)," and U.S. Provisional Patent Application Ser. No. 62/897,053 filed Sep. 6, 2019 entitled "DEEP LEARNING-ENABLED PREDICTION OF FERTILIZATION BASED ON OOCYTE MORPHOLOGICAL QUALITY." The entire content of each of these applications is hereby incorporated by reference in its entirety for all purposes.

RELATED APPLICATIONS

The present application claims priority to each of U.S. Provisional Patent Application Ser. No. 62/897,043 filed Sep. 6, 2019 entitled "DEEP NEURAL NETWORK-ENABLED EMBRYO TRACKING AND SPECIMEN IDENTIFICATION SYSTEM FOR ERROR MINIMIZATION IN IVF PRACTICES," U.S. Provisional Patent Application Ser. No. 62/897,045 filed Sep. 6, 2019 entitled "AUTOMATED QUALITY ASSESSMENT OF INDIVIDUAL EMBRYOLOGISTS PERFORMING ICSI USING DEEP LEARNING-ENABLED FERTILIZATION AND EMBRYO GRADING TECHNOLOGY," U.S. Provisional Patent Application Ser. No. 62/897,049 filed Sep. 6, 2019 entitled "MONITORING OF HUMAN EMBRYO CULTURE CONDITIONS USING A DEEP LEARNING-DERIVED KEY PERFORMANCE INDICATOR (KPI)," and U.S. Provisional Patent Application Ser. No. 62/897,053 filed Sep. 6, 2019 entitled "DEEP LEARNING-ENABLED PREDICTION OF FERTILIZATION BASED ON OOCYTE MORPHOLOGICAL QUALITY." The entire content of each of these applications is hereby incorporated by reference in its entirety for all purposes.

TECHNICAL FIELD

The present invention relates generally to the field of medical decision support, and more particularly to automated evaluation of quality assurance metrics for assisted reproduction procedures.

BACKGROUND OF THE INVENTION

Infertility is an underestimated healthcare problem that affects over forty-eight million couples globally and is a cause of distress, depression, and discrimination. Although assisted reproductive technologies (ART) such as in-vitro fertilization (IVF) has alleviated the burden of infertility to an extent, it has been inefficient with an average success rate of approximately twenty-six percent reported in 2015 in the US. IVF remains as an expensive solution, with a cost between $7000 and $20,000 per ART cycle in the US, which is generally not covered by insurance. Further, many patients require multiple cycles of IVF to achieve pregnancy.

Data analysis is a crucial part of an effective quality assessment (QA) program for an assisted reproductive procedure. Routine review of identified key performance indicators (KPIs) are important to ensure proper laboratory functioning and, perhaps more importantly, to identify potential problems to permit timely corrections. Fertilization assessment is the primary outcome used to measure embryology staff proficiency with Intracytoplasmic sperm injection (ICSI). However, tracking the developmental fate of ICSI derived embryos may provide a more complete picture of how well this procedure is being performed.

SUMMARY OF THE INVENTION

In accordance with an aspect of the present invention, a method is provided for assigning a quality parameter to a reproductive cellular structure. An image of the reproductive cellular structure is obtained. The image of the reproductive cellular structure is provided to a neural network to generate a value representing a morphology of the reproductive cellular structure. The value is compared to a predefined standard to provide a quality assurance metric representing one of a medical personnel, a facility, a growth medium, and an identity of the reproductive cellular structure.

In accordance with another aspect of the present invention, a system includes a processor, an output device, and a non-transitory computer readable medium storing machine executable instructions for assigning a quality assurance metric to an embryo. The machine executable instructions include an imager interface that receives an image of the embryo from an associated imager and a convolutional neural network that determines, from the image of the embryo, a value representing a likelihood of a successful outcome for the embryo. A quality analysis component calculates a value representing the performance of one of a medical professional, a facility, and a growth medium across a plurality of embryos and compares the value to a threshold value to generate the quality assurance metric. A user interface that displays the quality assurance metric to a user at the output device.

In accordance with yet another aspect of the present invention, a system includes a processor, an output device, and a non-transitory computer readable medium storing machine executable instructions for assigning a value representing a quality of an oocyte. The machine executable instructions include an imager interface that receives an image of the oocyte from an associated imager and a convolutional neural network that determines, from the image of the oocyte, a value representing one of a likelihood of successful fertilization of the oocyte and a location of the polar body of the oocyte. A user interface displays the value representing a likelihood of a successful fertilization of the oocyte to a user at the output device.

In accordance with still another aspect of the present invention, a system includes a processor, an output device, and a non-transitory computer readable medium storing machine executable instructions for confirming an identity of a reproductive cellular structure. The machine executable instructions include an imager interface that receives a first image of the reproductive cellular structure, taken at a first time, and a second image of the reproductive cellular structure, taken at a second time, from an associated imager. A neural network generates an identifier key from the first image of the reproductive cellular structure, and a value representing a morphology of the reproductive cellular structure from the second image. An identity verification component compares the value representing a morphology of the reproductive cellular structure to the identifier key to determine if the reproductive cellular structure belongs to a patient associated with the identifier key. A user interface displays the determination whether the reproductive cellular structure belongs to the patient associated with the identifier key to a user at the output device.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

A "reproductive cellular structure", as used herein, is an oocyte before or after fertilization. Accordingly, the term is intended to encompass both an oocyte and an embryo at any stage of development before implantation into a patient or subject.

A "quality assurance metric", as used herein, is a continuous, ordinal, or categorical value representing compliance with an established set of practices during an assisted reproductive procedure.

Current computer vision methods for embryo and oocyte assessment are semi-automated, limited to measuring specific parameters providing metrics that require further analysis by embryologists, and require strictly controlled imaging systems. Previous attempts in developing systems using machine-learning approaches in assisted reproduction have required intensive image preprocessing followed by human-directed segmentation of features for classification. Owing to the dependency of machine-learning approaches on image processing and segmentation, such methods suffer from the same limitations as computer vision techniques.

Here, we overcome this challenge by employing a deep neural networks pretrained with a large set of images for transfer learning classifications of reproductive cellular structures at clinically relevant stages of development. Unlike prior computer-aided algorithms used for assessment of reproductive cellular structures, the systems and methods provided herein allows for automated feature selection and analysis at the pixel level without any assistance by an embryologist. In one example, a convolutional neural network is applied to identify the shape, structure, and texture variations between morphologically complex reproductive cellular structures. The system is resilient to changes in image illumination and quality due to data acquisition using multiple instruments.

Figure 1:
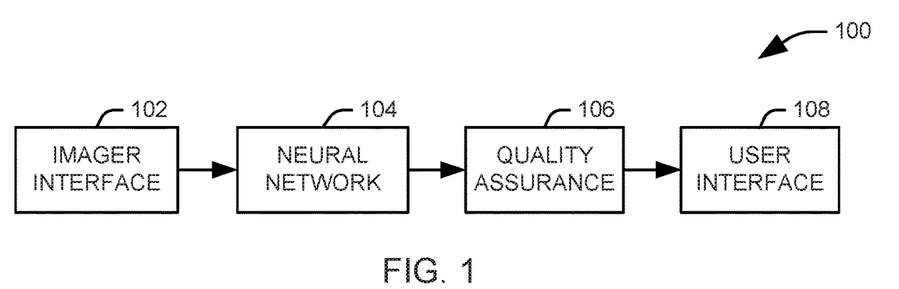
FIG. 1 illustrates a system for assigning a quality assurance metric to a reproductive cellular structure.

FIG. 1 illustrates a system 100 for assigning a quality assurance metric to a reproductive cellular structure. The system 100 includes an imager 102 that acquires an image of the reproductive cellular structure. For example, the imager 102 can include one or more cameras, capable of producing images in the visible or infrared range, paired with appropriate optics to provide an image of a reproductive cellular structure. In practice, the imager 102 can be implemented to capture images of the reproductive cellular structure at multiple days of development as part of a time-lapse oocyte/embryo imaging system. In one implementation, the imager 102 includes an attachment for a mobile device that operates with a camera of the mobile device to provide the images of reproductive cellular structure. The housing for the attachment can be 3-D printed using polylactic acid with dimensions of 82×34×48 mm. An acrylic lens can be included in the housing to provided appropriate magnification for the images.

In another implementation, the imager 102 can be implemented as a stand-alone system with an optical housing that is 3-D printed from polylactic acid and overall dimensions of 62×92×175 mm. The housing contains an electronic circuit with a white light-emitting diode, a three-volt battery, and a single pole double-throw switch. The reproductive cellular structure is transilluminated, with a 10× Plan-Achromatic objective lens for image magnification and a complementary metal-oxide-semiconductor (CMOS) image sensor for image data acquisition. The CMOS sensor can be connected to a single-board computer to process the captured images. The imager 102 can be connected to a mobile device via a wireless connection (e.g., Wi-Fi, Bluetooth, or a similar connection) for data processing and visualization.

The one or more images obtained at the imager 102 are provided to a neural network 104 that calculates, from the image of the reproductive cellular structure, at least one output value representing a morphology of the reproductive cellular structure. For example, the output value can represent a quality of the reproductive cellular structure based upon the morphology of the reproductive cellular structure or a key identifying the embryo based upon its morphological features. It will be appreciated that the neural network can be implemented as software instructions stored on a non-transitory computer readable medium and executed by an associated processor. In one example, the neural network 104 can be implemented on a cloud computing system.

In one implementation, the neural network 104 can be a convolutional neural network, which is a feed-forward artificial neural network that includes convolutional layers, which effectively apply a convolution to the values at the preceding layer of the network to emphasize various sets of features within an image. In a convolutional layer, each neuron is connected only to a proper subset of the neurons in the preceding layer, referred to as the receptive field of the neuron. In the illustrated example, the convolutional neural network is implemented using the Xception architecture. In one implementation, at least one chromatic value (e.g., a value for an RGB color channel, a YCrCb color channel, or a grayscale brightness) associated with each pixel is provided as an initial input to the convolutional neural network.

In another implementation, the neural network 104 can be implemented as a recurrent neural network. In a recurrent neural network, the connections between nodes in the network are selected to form a directed graph along a sequence, allowing it to exhibit dynamic temporal behavior. In another implementation, the neural network 104 is implemented and trained as a discriminative network in a generative adversarial model, in which a generative neural network and the discriminative network provide mutual feedback to one another, such that the generative neural network produces increasingly sophisticated samples for the discriminative network to attempt to classify.

In yet another application, a graph neural network can be used. Graph neural networks are connectionist models that capture the dependence of graphs via message passing between the nodes of graphs. Unlike standard neural networks, graph neural networks retain a state that can represent information from its neighborhood with arbitrary depth. Graph neural networks are able to model the relationship between the nodes in a graph and produce a numeric representation. In still another implementation, an autoencoder-based neural network can be used. Autoencoders are unsupervised, generative models that train a neural network to represent input data in a useful form. In one implementation, an autoencoder can be trained to reconstruct the input layer at the output layer, with alternative representations of the data being generated in the hidden layers of the network.

The inventors have found that the predictive capability of the neural network 104 can be enhanced by using the neural network 104 in combination with another expert system (not shown). In practice, any of a variety of experts systems can be utilized in combination with a convolutional or recurrent neural network, including support vector machines, random forest, self-organized maps, fuzzy logic systems, data fusion processes, ensemble methods, rule based systems, genetic algorithms, and artificial neural networks. It will be appreciated that the additional expert system may be trained on features from multiple stages of embryonic development as well as with features that are external to the images, such as biometric parameters of an egg donor, a sperm donor, or a recipient of the embryo.

The output value from the neural network 104 can be provided to a quality assurance component 106 that compares the output value to a predefined standard to provide a quality assurance metric. The quality assurance metric can represent, for example, the performance of one of a medical personnel, a facility, and a growth medium in extracting and fertilizing an oocyte and incubating an embryo to a point of implantation, with the predefined standard representing a quality of the reproductive cellular structure. When used in this manner, the quality assurance metric can be used as a replacement for a measured outcome, such as a successful fertilization or pregnancy, that might take significant additional time to ascertain. It will be appreciated that, in this instance, descriptive statistics can be generated from a plurality of evaluated reproductive cellular structures to provide the quality assurance metric for a given medical personnel, facility, or growth medium.

In one implementation, the neural network 104 is trained on a plurality of images or image sets of oocytes, taken prior to fertilization, that are classified into either a first class, representing normal fertilization of the embryo, or a second class, representing an abnormal fertilization of the embryo. For the purpose of this application, a normally fertilized embryo is an embryo that contains two pronuclei and an abnormally fertilized embryo is an embryo with any other number of pronuclei. The output of the neural network can be a continuous value representing the quality of the embryo that can be compared to a threshold value to assign the fertilization as "successful" or "unsuccessful." Accordingly, in this implementation, the performance of an embryologist or facility performing an oocyte extraction procedure can be evaluated as a percentage of extracted oocytes expected to result in successful fertilization. Alternatively, the output of the neural network can be used to generate an expected percentage of successful fertilizations for the embryologist or facility in performing a fertilization procedure, such as intracytoplasmic sperm injection (ICSI), and the quality assurance metric can be determined by comparing this expected value to an actual success rate for the embryologist or facility.

In another implementation, the neural network 104 is trained on a plurality of images or image sets of embryos taken at a selected stage or stages of embryo development, that are classified as representing a successful pregnancy or as not representing a successful pregnancy. In one example, each embryo is represented by an image taken on a third day of embryo development, for example, at seventy hours after fertilization. The output of the neural network can be a continuous value representing the quality of the embryo that can be compared to a threshold value to assign the fertilization as "successful" or "unsuccessful." Accordingly, in this implementation, the performance of an embryologist or facility performing a fertilization procedure or a growth medium used to incubate an embryo can be evaluated as a percentage of fertilized oocytes expected to result in successful pregnancies. Alternatively, the output of the neural network can be used to generate an expected percentage of successful implantations for the embryologist, facility, or medium in performing an embryo implantation, and the quality metric can be determined by comparing this expected value to an actual success rate for the embryologist, medium, or facility.

In still another implementation, the output of the neural network 104 represents an identity of the reproductive cellular structure as an identifier key, based on features representing the morphology of the reproductive cellular structure. In this implementation, an image of the reproductive cellular structure taken at a first time can be provided to the neural network to produce a first identifier key, at which point the dish containing the reproductive cellular structure can be labeled with the provided identifier key. When it is desirable to confirm an identity of the embryo in the dish, for example, just before transfer to the recipient uterus, another image can be acquired and provided to the neural network to generate a second identifier key. The two keys can be compared to determine if the embryo is properly labeled, and this information can be provided to the user as the quality assurance metric. In one example, the first time can be one hundred thirteen hours after insemination, and the second time can be one hundred fifteen hours after insemination.

The quality assurance metric, and any associated values that may be of interest in assuring the quality of a facility, medical professional, or medium involved in an assisted reproduction process can be provided to a user at an associated user interface 108. For example, the user interface 108 can include at least an output device, such as a display, and appropriate software, stored on a non-transitory medium and executed by an associated processor, for receiving the output of the 'neural network 104 and presenting it at the output device. In one implementation, the user interface 108 can include a mobile device that communicates wirelessly with the neural network.

Figure 2:
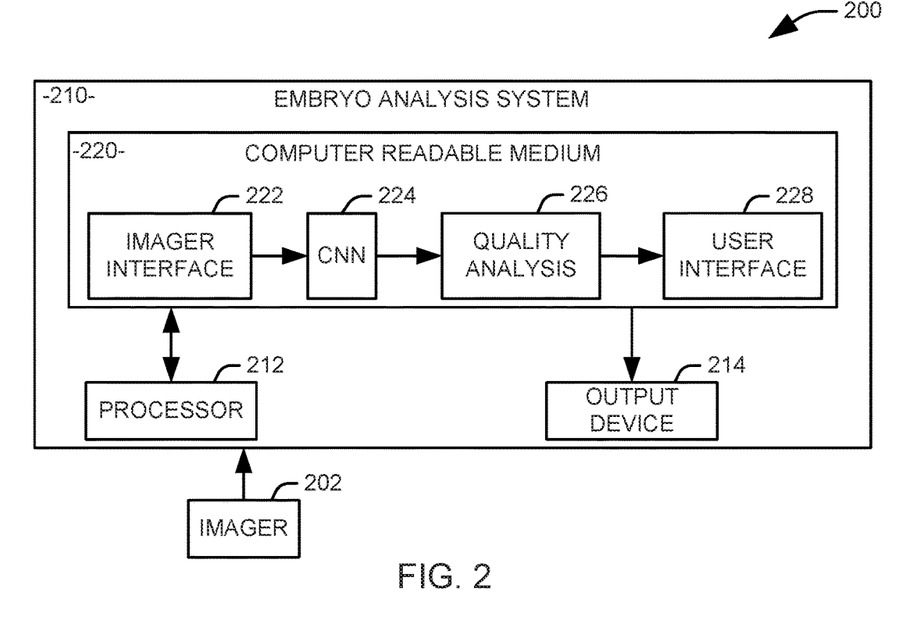
FIG. 2 provides an example implementation of a system for assigning a quality assurance metric to an embryo.

FIG. 2 provides an example implementation of a system 200 for assigning a quality assurance metric to an embryo. An important aspect of assisted reproductive technology is the condition of laboratory embryo cultures. The clinical outcome of an in-vitro fertilization (IVF) cycle is perhaps the best indicator of system efficiency with ongoing pregnancy rates providing the most robust marker of embryo quality. Several early developmental stage markers are widely used to monitor culture conditions; however, their association with clinical outcomes is unclear. Similarly, data analysis is a crucial part of an IVF quality assessment (QA) program. Routine review of identified key performance indicators (KPIs) are important to ensure proper laboratory functioning and, perhaps more importantly, to identify potential problems to permit timely corrections. Fertilization assessment is the primary outcome used to measure embryology staff proficiency with Intracytoplasmic sperm injection (ICSI). However, tracking the developmental fate of ICSI derived embryos may provide a more complete picture of how well this procedure is being performed. Current quality assessments require manual examination and recording of fertilization status and embryo developmental scores. These processes are labor-intensive and highly subjective in nature. Further, certain developmental metrics, such as pregnancy outcome results, are only available after a significant delay.

The illustrated system 200 can be used as an alternative method for monitoring KPIs for facilities, personnel, and growth media in the IVF laboratory without the need for manual assistance. This system can also be used to detect differences in implantation potential of developing embryos. The ability to accurately predict embryo implantation allows a practice to detect and correct variances in culture conditions and technical proficiencies several weeks faster than those relying on pregnancy outcome results. In the illustrated example, the quality assurance metric is a categorical parameter representing the expected success of implantation of the embryo given its morphological features. Quality assurance metrics for a plurality of embryos can be used to assess the impact of a given medical professional, growth medium, or facility on the quality of the embryo and allow for deficiencies in any of these factors to be remedied. For example, where a growth medium is providing a percentage of high-quality embryos that is below a threshold value, the growth medium can be replaced. Where an embryologist or facility performing fertilization procedures, such as ICSI, is providing a percentage of high-quality embryos that is below the threshold value, the embryologist or the personnel at the facility can be retrained or subjected to additional supervision.

In this example, the system 200 includes an imager 202 that acquires an image of each embryo on a third day of development. It will be appreciated, however, that the specific time at which the images of the embryos are captured can be varied based on a desired application, and in some implementations, multiple images are captured at various stages of development to provide a set of images for each embryo. For example, in one implementation, images captured on the first day of development can be used to evaluate the embryos, particularly where the performance of a medical personnel or facility in a fertilization process is being accessed. The imager 202 can be implemented in a manner similar to the imager 102 described in FIG. 1. The images captured at the imager 202 can be provided to an embryo analysis system 210.

The embryo analysis system 210 includes a processor 212, an output device 214, such as a display, and a non-transitory computer readable medium 220 storing executable instructions for providing a quality assurance metric representing a performance of a medical professional, a facility, or a growth medium. The executable instructions include an imager interface 222 that receives images from the imager 202 and provides them to a convolutional neural network 224 in an appropriate form for analysis.

In one implementation, a training set of embryo images can be generated from images or sets of images representing each embryo and a known outcome of the implantation of the embryo and used to train the convolutional neural network 224, such that an output for each image is a key performance indicator value representing the likelihood that implantation of the embryo will result in a successful outcome. In the illustrated implementation, the successful outcome is a successful pregnancy, but in some implementations, the successful outcome can be development of the embryo into a blastocyst or achieving a selected grade for the embryo at a selected point of development, such as a fifth day of development. It will be appreciated that the features for each embryo can include values external to the image, such as biometric parameters of the patient, as well as the image provided to the convolutional neural network 224. In one example, the value output by the convolutional neural network 224 can be a continuous value representing the likelihood of a successful pregnancy or a categorical value representing one or more ranges of likelihood. For example, the key performance indicator can be represented as a categorical parameter that can assume a first value, indicating that a successful pregnancy is likely upon implantation, and a second value, indicating that a successful pregnancy is not likely.

The output of the convolutional neural network 224 is provided to a quality analysis component 226 that evaluates the performance of the medical professional, facility, or growth medium. In the illustrated example, the quality analysis component 226 maintains a running average over a defined window representing either an average of the key performance indicator values across embryos in the defined window or a percentage of embryos that have been indicated by the convolutional neural network as likely to result in a successful pregnancy. For example, the running average can be maintained over a defined period of time or a defined number of embryos generated. The quality analysis component 226 can monitor this running average and determine whether it meets a predefined threshold value to provide the quality assurance metric. For example, the predefined threshold value for successful pregnancies can be fifty percent.

In one example, the quality assurance metric is a categorical value that assumes a first value when the running average exceeds the threshold and a second value when the running average falls below the threshold. In another example, the quality assurance value maintains the first value until the running average has fallen below a threshold value for a predetermined amount of time or number of implantations. The quality assurance metric and any other values of interest, such as the running average, can be provided to a user at the output device 214 via an associated user interface 228. In one example, an alert can be provided to the user via a local or wide area network connection as an e-mail, SMS message, or similar communication whenever the quality assurance value changes from the first value to the second value.

Figure 3:
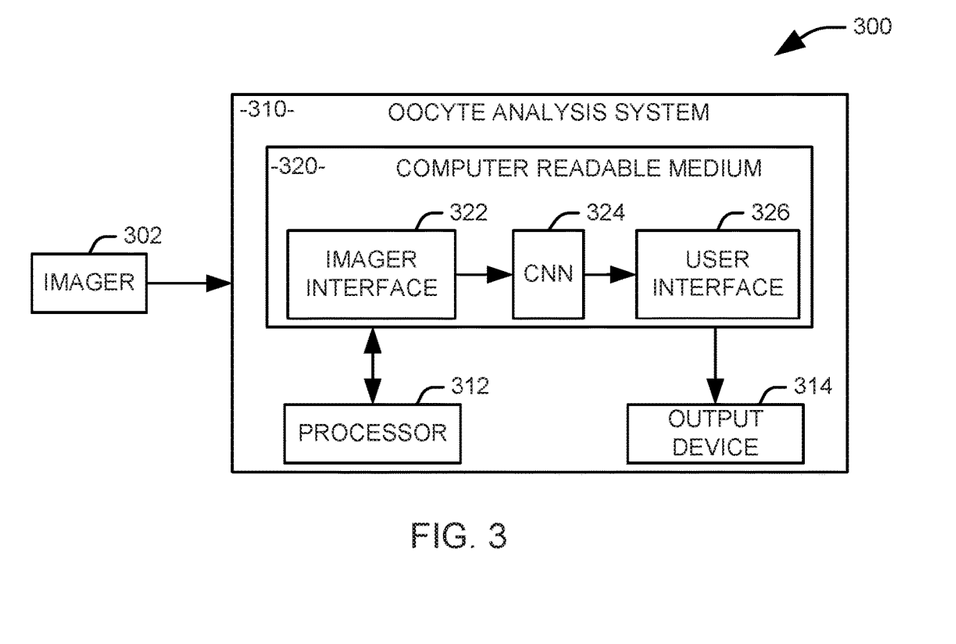
FIG. 3 provides an example implementation of a system for assigning a quality metric to an oocyte.

FIG. 3 provides an example implementation of a system 300 for assigning a quality metric to an oocyte. Failure to fertilize oocytes can be associated with both the male and female factors. However, for certain women, especially those with premature ovarian failure, diminished ovarian reserves, or genetically transmittable diseases, donor egg may be the only available option in giving birth to a healthy child. Addition of donor eggs to a cycle significantly increases the patient's out-of-pocket costs. Obtaining premium quality eggs that have a high chance of success may help reduce the uncertainty in patients, while potentially improving rates of pregnancy. Currently, there is no objective system that can evaluate oocyte quality and predict its developmental potential. The illustrated system 300 can be used to accurately predict the fertilization potential of oocytes and thus allow for selection of the highest quality oocytes for fertilization and implantation. It can also be used to evaluate the performance of a facility or embryologist in a fertilization process by comparing a performance of the facility or embryologist to an expected rate of success given the predicted fertilization potential of the oocytes used. In the illustrated example, the system 300 can produce a continuous parameter representing the expected success of fertilization of the oocyte given its morphological features.

The system 300 includes an imager 302 that acquires an image of each oocyte prior to fertilization. The imager 302 can be implemented in a manner similar to the imager 102 described in FIG. 1. The images captured at the imager 302 can be provided to an oocyte analysis system 310 that includes a processor 312, an output device 314, such as a display, and a non-transitory computer readable medium 320 storing executable instructions for providing a value representing the fertilization potential of an oocyte. The executable instructions include an imager interface 322 that receives images from the imager 302 and provides them to a convolutional neural network 324 in an appropriate form for analysis.

In one implementation, a training set of oocyte images can be generated from image or images representing each oocyte and a known fertilization outcome for the oocyte and used to train the convolutional neural network 324, such that an output for each image is a value representing the likelihood that fertilization of the oocyte will result in a successful outcome. In the illustrated implementation, the fertilization outcome for each training image is determined at eighteen hours after insemination. It will be appreciated that the features for each embryo can include values external to the image, such as biometric parameters of the donor of the oocytes, as well as the extracted features from the convolutional neural network 324. It will be appreciated that the value output by the convolutional neural network 324 can be a continuous value representing the likelihood of a successful fertilization or a categorical value representing one or more ranges of likelihood. In one example, the value output by the convolutional neural network 324 is a categorical parameter that can assume a first value, indicating that a successful fertilization is likely, and a second value, indicating that a successful fertilization is not likely. The output of the convolutional neural network 324 is provided to a user at the output device 314 via an associated user interface 326.

In another implementation, the output of the convolutional neural network 324 can represent a location of the polar body on an oocyte. Intracytoplasmic sperm injection is a procedure that includes alignment of metaphase (MII) oocytes, selection and immobilization of sperm, and injection of sperm at a precise location that does not interfere with the mitotic spindle. The spindle is located adjacent to the extruded polar body and cannot be visualized using bright field microscopy. Therefore, it is standard practice to align oocytes based on the location of the polar body and to inject sperm ninety degrees from this visible structure. In this implementation, the convolutional neural network is trained on a plurality of images of oocytes having a known location of the polar body labeled with classes representing discrete sections of the imaged oocyte. In one example, twelve classes are used, with each representing a thirty-degree section of the imaged oocyte. The output of the convolutional neural network for a novel images is the class representing the section in which the polar body is located.

Figure 4:
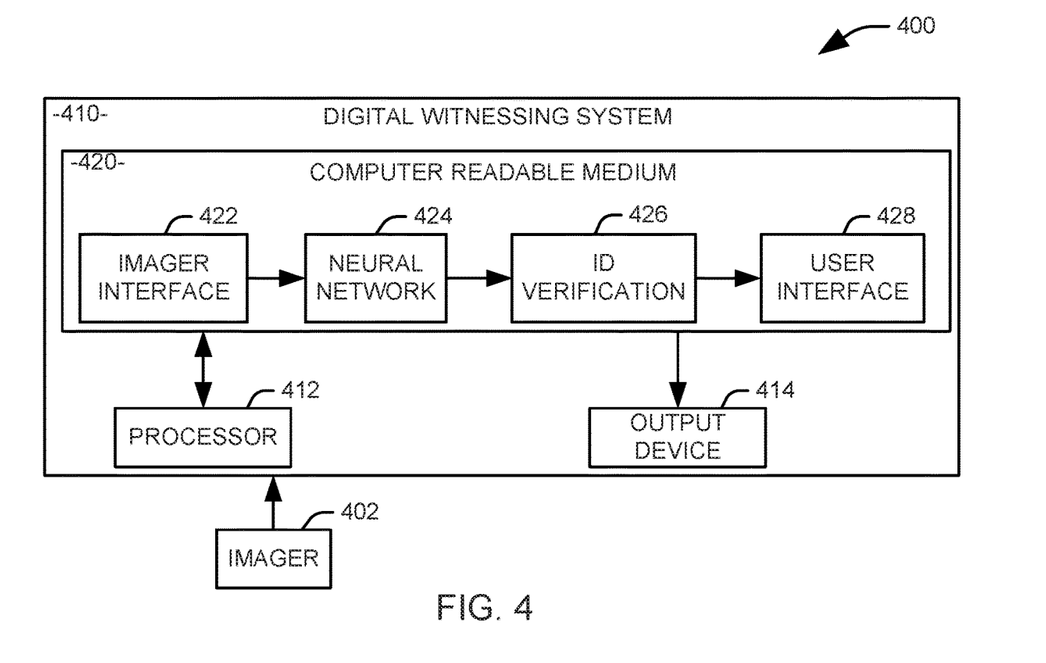
FIG. 4 illustrates an example implementation of a system for verifying an identity of a reproductive cellular structure.

FIG. 4 illustrates an example implementation of a system 400 for verifying an identity of an embryo. The use of electronic witnessing systems is a recommended practice in IVF labs to improve traceability and in reduce incidents in which an incorrect embryo is implanted into a patient. Such errors are difficult to detect, and generally become apparent primarily when couples give birth to babies of a visibly different genetic makeup than their own. The actual number of errors is therefore difficult to estimate, and a biological sample misidentification of this sort could potentially be catastrophic for the clinic, clinic staff, and especially patients. IVF labs are concerned about legal liability and witnessing systems can play a vital role in minimizing identification errors.

The illustrated system 400 makes use of a multi-level traceability system employing a hardware-based radio frequency identification (RFID) tag combined with a software-based deep convolutional neural network that recognizes the unique morphological features in a patient's oocytes and embryos. To this end, the system 400 includes an imager 402 that acquires an image of a reproductive cellular structure at a specific stage of development. It will be appreciated that the specific time at which the images of the reproductive cellular structures are captured can be varied based on a desired application, and in some implementations, multiple images are captured at various stages of development to provide a set of images for each reproductive cellular structure. The imager 402 can be implemented in a manner similar to the imager 102 described in FIG. 1. The images captured at the imager 402 can be provided to a digital witnessing system 410.

The digital witnessing system 410 includes a processor 412, an output device 414, such as a display, and a non-transitory computer readable medium 420 storing executable instructions for verifying an identity of an embryo or oocyte. The executable instructions include an imager interface 422 that receives images from the imager 402 and provides them to a neural network 424 in an appropriate form for analysis. The neural network can be implemented, for example, as a convolutional neural network, a graph neural network, and autoencoder-based neural network, or a generative adversarial neural network. In one implementation, the neural network 424 can be pretrained on a set of images to provide morphological features from a provided image, such that the output associated with a given image of an embryo or oocyte is an identifier key representing the morphology of the embryo or oocyte. The morphology of the embryo or oocyte can be stable over various periods of development, such that an identifier key produced from an image taken at a first time would be expected to match an identifier key produced from an image taken at a second time. In one example, an identifier key can be produced for a given reproductive cellular structure at a first time and affixed to a dish containing the reproductive cellular structure, for example, by encoding the identifier key in an RFID tag attached to the dish.

An identity verification component 426 compares two identifier keys to determine if they represent the same reproductive cellular structure. In one example, a second identifier key can be generated at key points in the assisted reproduction process, such as immediately before fertilization of an oocyte or immediately before transfer of an embryo into a patient. The identity verification component 426 can produce a quality assurance metric representing the likelihood that the second identifier key represents a same reproductive cellular structure as the first identifier key, and thus a patient associated with the first identifier key. In one example, the quality assurance metric is categorical, with a first value representing a match between the first identifier key and the second identifier key and the second value representing a failure of the first identifier key to match the second identifier key. Alternatively, the quality assurance metric can be a continuous value representing the likelihood that the two keys represent the same embryo. The quality assurance metric can be provided to a user at the output device 414 via an associated user interface 428. In one example, an alert can be provided to the user via a local or wide area network connection as an e-mail, SMS message, or similar communication whenever the quality assurance value assumes a value representing a misidentification of a reproductive cellular structure as belonging to a wrong patient.

In view of the foregoing structural and functional features described above, methods in accordance with various aspects of the present invention will be better appreciated with reference to FIGS. 5-8. While, for purposes of simplicity of explanation, the methods of FIGS. 5-8 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

Figure 5:
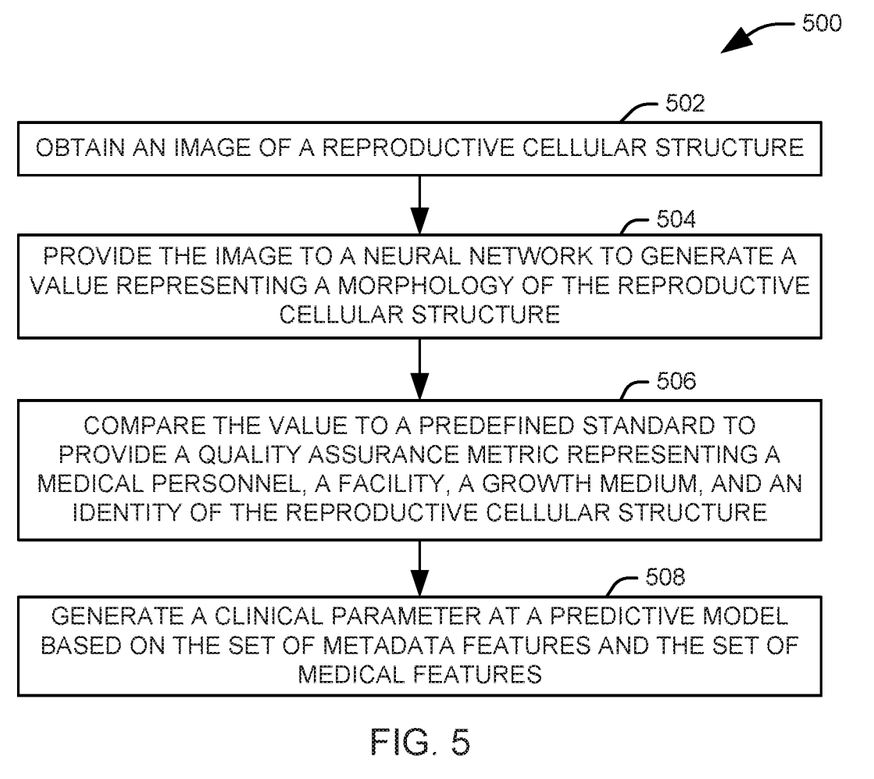
FIG. 5 illustrates a method for assigning a quality assurance metric to a reproductive cellular structure.

FIG. 5 illustrates a method 500 for assigning a quality assurance metric to a reproductive cellular structure. At 502, an image of the reproductive cellular structure is obtained. In practice, each reproductive cellular structure can be represented by a set of one or more images taken at various times during the development of the reproductive cellular structure, including, for example, prior to fertilization, during a first day of embryo development, during a third day of embryo development, during a fifth day of embryo development, and immediately prior to implantation of an embryo. In general, the images are obtained via visible light microscopy, although other forms of imaging could be employed, depending on the application.

At 504, the image of the reproductive cellular structure is provided to a neural network to generate a value representing a morphology of the reproductive cellular structure. In one implementation, the neural network is a convolutional neural network. In other implementations, the neural network can be a generative adversarial neural network, a graph neural network, or an autoencoder-based neural network. In some examples, the steps at 502 and 504 can be repeated to provide respective values representing the morphology of a plurality of reproductive cellular structures. Further, in some examples, a set of multiple images can be acquired for each reproductive cellular structure and provided to the neural network, with each of the set of multiple images representing the reproductive cellular structure at different stages of development.

At 506, the value representing the morphology of a plurality of reproductive cellular structures is comparted to a predefined standard to provide a quality assurance metric representing one of a medical personnel, a facility, a growth medium, and an identity of the reproductive cellular structure. In one example, the predefined standard is determined by obtaining a second image of the reproductive cellular structure at a time before the image is acquired at 506 and providing the second image to the neural network to provide the predefined standard as an identifier key for the reproductive cellular structure. This identifier key can then be encoded on a radio frequency identification (RFID) tag and affixed to a dish in which the reproductive cellular structure is stored. In one implementation, the quality assurance metric is a categorical value having a first value, indicating that the first image and the second image represent a same reproductive cellular structure, when the unique key matches the predefined standard, and a second value, indicating that the first image and the second image represent different reproductive cellular structures, when the unique key does not match the predefined standard.

In another example, a representative value can be generated from a plurality of values representing the morphology of a plurality of reproductive cellular structures, and this representative value is compared to the predefined standard. In one example, each of the plurality of reproductive cellular structures can be embryos that are the result of a fertilization process performed by a given embryologist or performed at a given facility, and each value representing the morphology of a given reproductive cellular structure represents an likelihood that implantation of the embryo will result in a successful pregnancy. The representative value can represent a percentage of the plurality of embryos that have been indicated as likely to result in a successful pregnancy, and the quality assurance metric can be a categorical value that assumes a first value when the percentage is above a threshold and assumes a second value when the percentage is below a threshold. In one example, a user can be altered when the quality assurance metric transitions from the first value to the second value.

Similarly, each of the plurality of reproductive cellular structures can be embryos that are cultured in a given growth medium, and each value representing the morphology of a given reproductive cellular structure represents a likelihood that implantation of the embryo will result in a successful pregnancy. The representative value can represent a percentage of the plurality of embryos that have been indicated as likely to result in a successful pregnancy, and the quality assurance metric can be a categorical value that assumes a first value when the percentage is above a threshold and assumes a second value when the percentage is below a threshold. In one example, a user can be altered when the quality assurance metric transitions from the first value to the second value. The quality assurance metric can be displayed to a user at 508.

Figure 6:
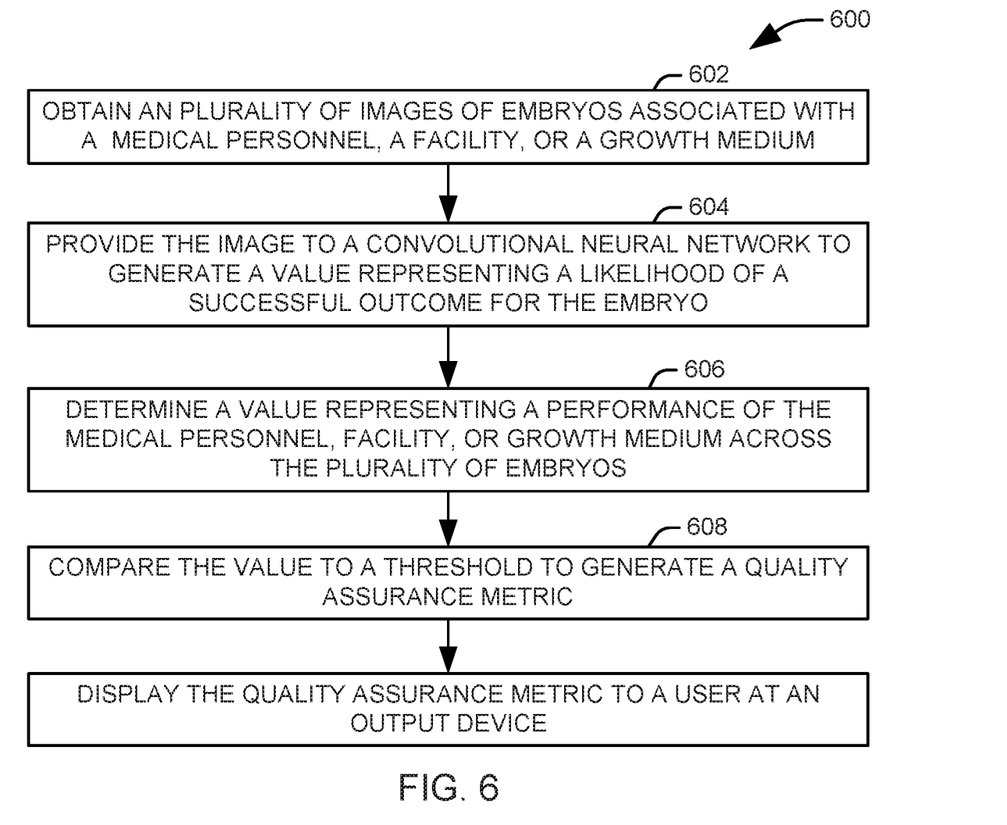
FIG. 6 illustrates a method for assigning a quality assurance metric to an embryo.

FIG. 6 illustrates a method 600 for assigning a quality assurance metric to an embryo. At 602, a plurality of images of a respective plurality of embryos associated with either a medical professional, a facility, or a growth medium is obtained. For example, the plurality of embryos can all be fertilized by a given embryologist or at a given facility, or cultured in a same growth medium. Each embryo can be represented by a set of one or more images taken at various times during the development of the embryo, including, for example, a first day of embryo development and a third day of embryo. In general, the images are obtained via visible light microscopy, although other forms of imaging could be employed, depending on the application. At 604, each of the plurality of images is provided to a convolutional neural network to generate a respective plurality of values representing a likelihood of a successful outcome for the embryo, for example, development to a blastocyst, achievement of a specific grade on the fifth day of development, or a successful pregnancy upon implantation. In some examples, a set of multiple images can be acquired for each reproductive cellular structure and provided to the neural network, with each of the set of multiple images representing the reproductive cellular structure at different stages of development.

At 606, a value representing the performance of the one of a medical professional, a facility, and a growth medium is determined across the plurality of embryos from the plurality of values representing the likelihood of a successful outcome for the embryo. In one example, each of the plurality of values is a categorical parameter representing ranges of likelihood for a successful outcome, and a percentage of the values representing a given category is generated as the representative value. In another example, each of the plurality of values is a continuous parameter, and the representative value is an average (e.g., mean or median) across the plurality of values. At 608, the compares the value to a threshold value to generate the quality assurance metric. For example, the quality assurance metric can assume a first value when the representative value exceeds the threshold value and assume a second value when the representative value does not exceed the threshold value. The quality assurance metric is displayed to a user at an output device at 610.

Figure 7:
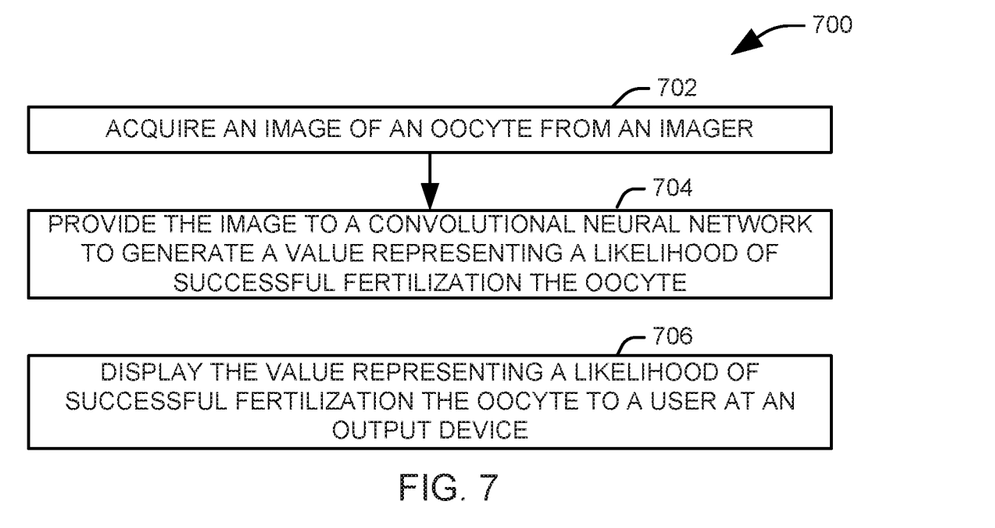
FIG. 7 illustrates a method for assigning a value representing a quality of an oocyte.

FIG. 7 illustrates a method 700 for assigning a value representing a quality of an oocyte. At 702, an image of the oocyte is acquired from an associated imager. In general, the image is obtained via visible light microscopy, although other forms of imaging could be employed, depending on the application. At 704, the image is provided to a convolutional neural network that determines, from the image of the oocyte, a value representing a likelihood of a successful fertilization of the oocyte. In one example, the convolutional neural network was trained on images of oocytes having known outcomes and labelled with a fertilization status of an embryo resulting from fertilization of the oocyte at eighteen hours after insemination. At 706, the value representing a likelihood of a successful fertilization of the oocyte is displayed to a user at an output device.

Figure 8:
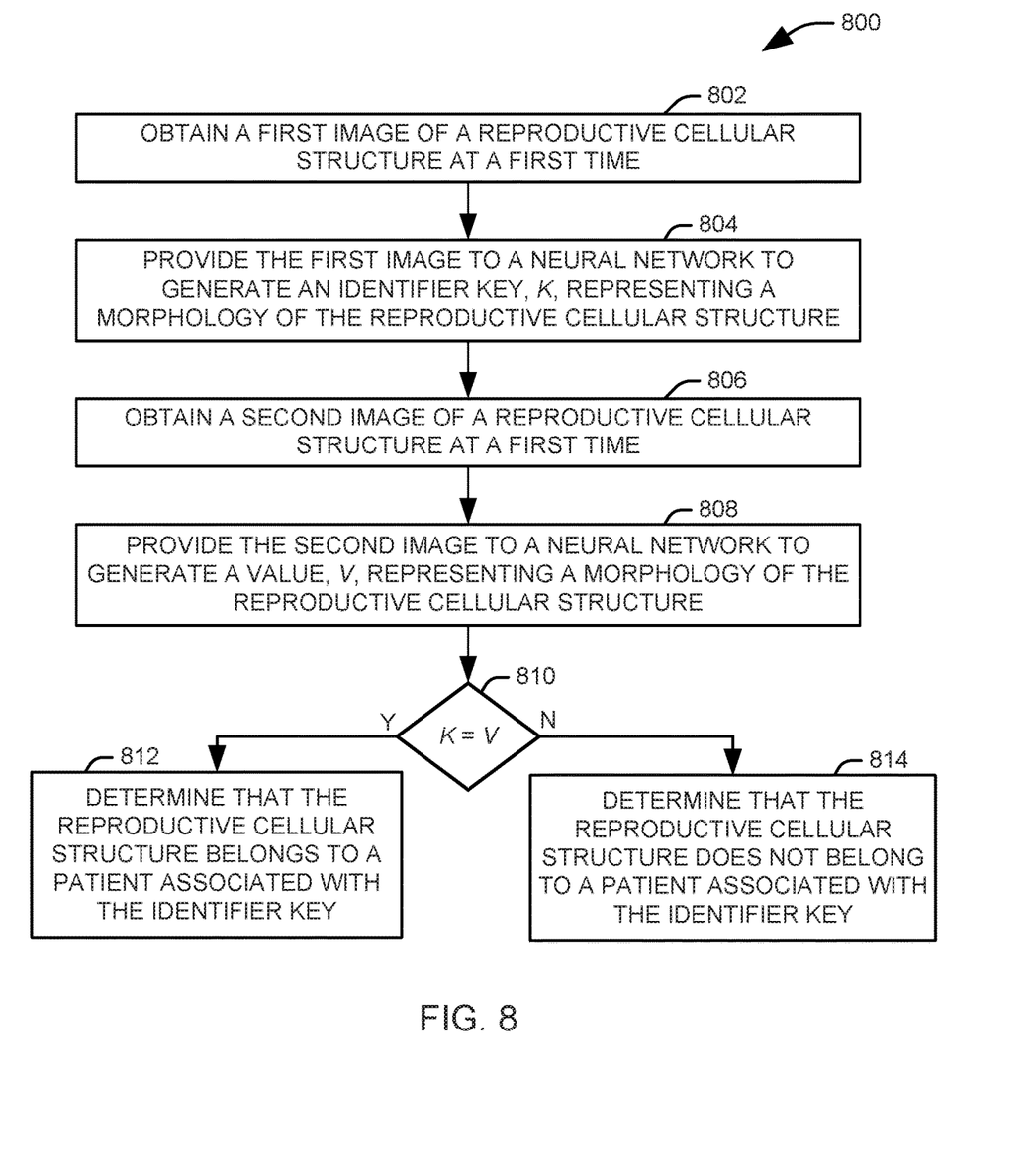
FIG. 8 illustrates a method for verifying an identity of a reproductive cellular structure.

FIG. 8 illustrates a method 800 for verifying an identity of a reproductive cellular structure. At 802, a first image of the reproductive cellular structure is obtained at a first time. In practice, each reproductive cellular structure can be represented by a set of one or more images taken at various times during the development of the reproductive cellular structure, including, for example, prior to fertilization, during a first day of embryo development, during a third day of embryo development, during a fifth day of embryo development, and immediately prior to implantation of an embryo. At 804, the first image is provided to a neural network to provide an identifier key, K, representing the morphology of the reproductive cellular structure. In one example, the neural network is a convolutional neural network. In another example, the neural network is either a generative adversarial neural network, a graph neural network, or an autoencoder-based neural network.

At 806, a second image of the reproductive cellular structure is obtained at a second time. At 808, the second image is provided to a neural network to provide a value, V, representing the morphology of the reproductive cellular structure. At 810, it is determined if the value matches the identifier key. If so (Y), it is determined at that 812 that the reproductive cellular structure belongs to a patient associated with the identifier key. If not (N), it is determined at 814 that the reproductive cellular structure does not belong to the patient associated with the identifier key and that an error has likely been made.

Figure 9:
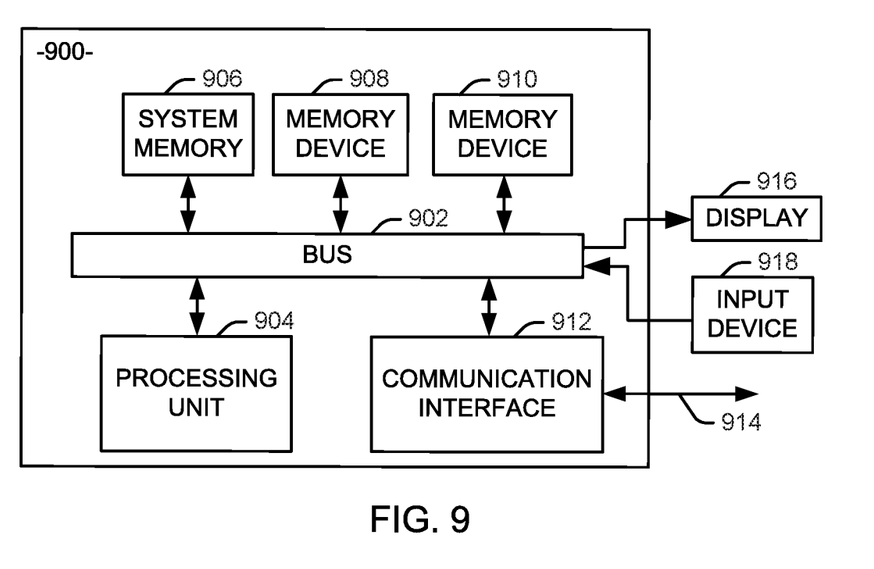
FIG. 9 is a schematic block diagram illustrating an exemplary system of hardware components capable of implementing examples of the systems and methods disclosed herein.

FIG. 9 is a schematic block diagram illustrating an exemplary system 900 of hardware components capable of implementing examples of the systems and methods disclosed in FIGS. 1-8, such as the system for assigning a quality assurance metric to a reproductive cellular structure illustrated in FIG. 1. The system 900 can include various systems and subsystems. The system 900 can be any of personal computer, a laptop computer, a workstation, a computer system, an appliance, an application-specific integrated circuit (ASIC), a server, a server blade center, or a server farm.

The system 900 can includes a system bus 902, a processing unit 904, a system memory 906, memory devices 908 and 910, a communication interface 912 (e.g., a network interface), a communication link 914, a display 916 (e.g., a video screen), and an input device 918 (e.g., a keyboard and/or a mouse). The system bus 902 can be in communication with the processing unit 904 and the system memory 906. The additional memory devices 908 and 910, such as a hard disk drive, server, stand-alone database, or other non-volatile memory, can also be in communication with the system bus 902. The system bus 902 interconnects the processing unit 904, the memory devices 906-910, the communication interface 912, the display 916, and the input device 918. In some examples, the system bus 902 also interconnects an additional port (not shown), such as a universal serial bus (USB) port.

The system 900 could be implemented in a computing cloud. In such a situation, features of the system 900, such as the processing unit 904, the communication interface 912, and the memory devices 908 and 910 could be representative of a single instance of hardware or multiple instances of hardware with applications executing across the multiple of instances (i.e., distributed) of hardware (e.g., computers, routers, memory, processors, or a combination thereof). Alternatively, the system 900 could be implemented on a single dedicated server.

The processing unit 904 can be a computing device and can include an application-specific integrated circuit (ASIC). The processing unit 904 executes a set of instructions to implement the operations of examples disclosed herein. The processing unit can include a processing core.

The additional memory devices 906, 908, and 910 can store data, programs, instructions, database queries in text or compiled form, and any other information that can be needed to operate a computer. The memories 906, 908 and 910 can be implemented as computer-readable media (integrated or removable) such as a memory card, disk drive, compact disk (CD), or server accessible over a network. In certain examples, the memories 906, 908 and 910 can comprise text, images, video, and/or audio, portions of which can be available in formats comprehensible to human beings.

Additionally or alternatively, the system 900 can access an external data source or query source through the communication interface 912, which can communicate with the system bus 902 and the communication link 914.

In operation, the system 900 can be used to implement one or more parts of a system for assigning a quality assurance metric to a reproductive cellular structure in accordance with the present invention. Computer executable logic for implementing the quality assurance system resides on one or more of the system memory 906, and the memory devices 908, 910 in accordance with certain examples. The processing unit 904 executes one or more computer executable instructions originating from the system memory 906 and the memory devices 908 and 910. It will be appreciated that a computer readable medium can include multiple computer readable media each operatively connected to the processing unit.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, and volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The terms "computer readable medium" and "machine readable medium" includes, but is not limited to portable or fixed storage devices, optical storage devices, wireless channels, and/or various other storage mediums capable of storing that contain or carry instruction(s) and/or data. It will be appreciated that a "computer readable medium" or "machine readable medium" can include multiple media each operatively connected to a processing unit.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

Having Described the Invention, We claim:

1. A method for assigning a quality parameter to a reproductive cellular structure, comprising:
   obtaining an image of the reproductive cellular structure;
   providing the image of the reproductive cellular structure to a neural network to generate a value representing a morphology of the reproductive cellular structure;
   comparing the value to a predefined standard to provide a quality assurance metric representing one of a medical personnel, a facility, a growth medium, and an identity of the reproductive cellular structure.

2. The method of claim 1, wherein obtaining the image of the reproductive cellular structure comprises obtaining a plurality of images representing the reproductive cellular structure and providing the image of the reproductive cellular structure to the neural network comprises providing each of the plurality of images to the neural network to generate a plurality of values representing the morphology of the plurality of reproductive cellular structures.

3. The method of claim 2, further comprising generating a representative value from the plurality of values representing the morphology of the plurality of reproductive cellular structures and comparing the representative value to the predefined standard.

4. The method of claim 3, wherein the reproductive cellular structure is an embryo, and the representative value represents a likelihood that implantation of the embryo will result in a successful pregnancy.

5. The method of claim 1, wherein obtaining the image of the reproductive cellular structure comprises obtaining a plurality of images representing a respective plurality of reproductive cellular structures and providing the image of the reproductive cellular structure to the neural network comprises providing each of the plurality of images to the neural network to generate a plurality of values representing the morphology of the plurality of reproductive cellular structures.

6. A method for assigning a quality parameter to a reproductive cellular structure, comprising:
   obtaining a plurality of images representing a respective plurality of embryos;
   providing each of the plurality of images to a neural network to generate a plurality of values representing morphologies of the reproductive cellular structures, each of the plurality of values representing the likelihood that implantation of their respective embryo will result in a successful pregnancy; and comparing the value to a predefined standard to provide a quality assurance metric representing one of a medical personnel, a facility, a growth medium, and an identity of the reproductive cellular structure.

* * * * *